(12) United States Patent
Wada et al.

(10) Patent No.: US 9,733,220 B2
(45) Date of Patent: Aug. 15, 2017

(54) ULTRASOUND PROBE AND METHOD OF PRODUCING THE SAME

(71) Applicant: FUJIFILM Corporation, Tokyo (JP)

(72) Inventors: Takatsugu Wada, Ashigara-kami-gun (JP); Atsushi Osawa, Ashigara-kami-gun (JP); Katsuya Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 471 days.

(21) Appl. No.: 14/452,659

(22) Filed: Aug. 6, 2014

(65) Prior Publication Data

US 2014/0338455 A1 Nov. 20, 2014

Related U.S. Application Data

(63) Continuation of application No. PCT/JP2013/052714, filed on Feb. 6, 2013.

(30) Foreign Application Priority Data

Feb. 7, 2012 (JP) .................................. 2012-023924
Nov. 6, 2012 (JP) .................................. 2012-244343

(51) Int. Cl.
*G01N 29/07* (2006.01)
*G01N 29/24* (2006.01)
(Continued)

(52) U.S. Cl.
CPC ....... *G01N 29/2437* (2013.01); *A61B 5/0095* (2013.01); *A61B 8/4444* (2013.01);
(Continued)

(58) Field of Classification Search
CPC .. G01N 29/2437; G01N 29/06; G01N 29/245; A61B 8/4444; B06B 1/0622; H01L 41/25; Y10T 29/42
(Continued)

(56) References Cited

U.S. PATENT DOCUMENTS

2008/0021328 A1   1/2008 Habu et al.
2010/0244812 A1   9/2010 Sasaki
(Continued)

FOREIGN PATENT DOCUMENTS

CN   1555764 A    12/2004
EP   2143381 A1    1/2010
(Continued)

OTHER PUBLICATIONS

Partial translation of the Chinese Office Action, dated Jul. 2, 2015, for Chinese Application No. 201380008464.0.
(Continued)

*Primary Examiner* — Laura Martin
*Assistant Examiner* — Rose M Miller
(74) *Attorney, Agent, or Firm* — Birch, Stewart, Kolasch & Birch, LLP (57) ABSTRACT

An ultrasound probe comprises: a backing material; a plurality of inorganic piezoelectric elements arranged on a top surface of the backing material; a first acoustic matching layer separated into a plurality of pieces disposed on the plurality of inorganic piezoelectric elements; and a second acoustic matching layer separated into a plurality of pieces disposed on the first acoustic matching layer, wherein the second acoustic matching layer comprises an upper organic layer constituting a plurality of organic piezoelectric elements, and a lower organic layer for performing, together with the upper organic layer, acoustic matching for the plurality of inorganic piezoelectric elements.

18 Claims, 3 Drawing Sheets

(51) Int. Cl.
  *B06B 1/06*   (2006.01)
  *A61B 8/00*   (2006.01)
  *G01N 29/06*  (2006.01)
  *H01L 41/25*  (2013.01)
  *A61B 5/00*   (2006.01)

(52) U.S. Cl.
  CPC ........... *B06B 1/0622* (2013.01); *G01N 29/06* (2013.01); *H01L 41/25* (2013.01); *Y10T 29/42* (2015.01)

(58) Field of Classification Search
  USPC .................................. 73/627, 628, 632, 641
  See application file for complete search history.

(56)  References Cited

U.S. PATENT DOCUMENTS

| | | |
|---|---|---|
| 2011/0062824 A1 | 3/2011 | Wada |
| 2011/0198968 A1* | 8/2011 | Sato ..................... A61B 8/4483 310/317 |
| 2011/0257532 A1 | 10/2011 | Sasaki |

FOREIGN PATENT DOCUMENTS

| | | |
|---|---|---|
| EP | 2295154 A1 | 3/2011 |
| JP | 5-277102 A | 10/1993 |
| JP | 2009-268807 A | 11/2009 |
| JP | 2011-45514 A | 3/2011 |
| JP | 2011-67485 A | 4/2011 |
| JP | 2011-83362 A | 4/2011 |
| JP | 2012-11024 A | 1/2012 |
| WO | WO 2008/010509 A1 | 1/2008 |

OTHER PUBLICATIONS

Decision of Refusal issued in the corresponding Japanese Patent Application No. 2012-244343 on Sep. 29, 2015.

European Office Communication, dated May 12, 2016, for European Application No. 13 746 281.8.

Japanese Office Action, dated Mar. 31, 2015, for Japanese Application No. 2012-244343, with an English translation thereof.

The International Preliminary Report on Patentability and the English translation of the Written Opinion of the International Searching Authority, dated Aug. 21, 2014, for International Application No. PCT/JP2013/052714.

International Search Report issued in PCT/JP2013/052714, dated Mar. 5, 2013.

Extended European Search Report for European Application No. 13746281.8, dated Sep. 8, 2015.

* cited by examiner

ULTRASOUND PROBE AND METHOD OF PRODUCING THE SAME

CROSS-REFERENCE TO RELATED APPLICATIONS

This application is a Continuation of PCT International Application No. PCT/JP2013/052714 filed on Feb. 6, 2013, which claims priority under 35 U.S.C. §119(a) to Japanese Application No. 2012-023924 filed on Feb. 7, 2012 and Japanese Application No. 2012-244343 filed on Nov. 6, 2012. Each of the above application(s) is hereby expressly incorporated by reference, in its entirety, into the present application.

BACKGROUND OF THE INVENTION

The present invention relates to an ultrasound probe and a method of producing the same and in particular to an ultrasound probe comprising a plurality of layered inorganic and organic piezoelectric elements layered on each other and a method of producing the same.

Conventionally, ultrasound diagnostic apparatuses using ultrasound images have been employed in the medical field. Generally, an ultrasound diagnostic apparatus of this type transmits an ultrasonic beam from an ultrasound probe into a subject's body, receives the echo from the subject with the ultrasound probe, and electrically processes the resulting reception signals to produce an ultrasound image.

In recent years, it has been a mainstream to utilize harmonic imaging where a harmonic component, which is generated as the ultrasonic waveform deforms due to non-linearity of the subject, is received and visualized to give more accurate diagnosis. In addition, as a new diagnostic method using ultrasonic waves, attention has been paid to photoacoustic imaging in which a living body is irradiated with a laser, whereby a weak broadband elastic wave is generated due to adiabatic expansion to be received and visualized.

Ultrasound probes appropriate for use in harmonic imaging or photoacoustic imaging have been proposed, an example of which is disclosed by WO 2008/010509 and is formed of a plurality of inorganic piezoelectric elements using inorganic piezoelectric bodies made of lead zirconate titanate (Pb(Zr, Ti)0$_3$) or the like and a plurality of organic piezoelectric elements using organic piezoelectric bodies made of polyvinylidene fluoride (PVDF) or the like layered over each other.

The inorganic piezoelectric elements can transmit higher power ultrasonic beams, and the organic piezoelectric elements can sensitively receive harmonic signals. In addition, the inorganic piezoelectric elements can acquire a reception signal of an ordinary ultrasonic wave, and the organic piezoelectric elements can sensitively receive a broadband signal in photoacoustic imaging.

Ultrasonic beams outputted from the inorganic piezoelectric elements penetrate organic piezoelectric bodies and thereafter are emitted from the ultrasound probe into the subject's body. Hence, the thickness of the organic piezoelectric bodies is designed so as to improve the acoustic transmittance of the ultrasonic beams. In particular, the organic piezoelectric bodies are designed to have a thickness which is near the value satisfying the $\lambda/4$ resonance condition when the fundamental waves from the inorganic piezoelectric elements have a wavelength $\lambda$. Accordingly, the organic piezoelectric bodies cannot conventionally be freely designed to have an arbitrary thickness but had to be designed to have a certain thickness in order to satisfy the above-described resonance condition. On the other hand, since the organic piezoelectric body has a small relative permittivity, if the organic piezoelectric elements are formed to be thick, the electrical capacitance thereof becomes small. Hence, it has been difficult for a circuit to efficiently acquire a reception signal generated by an ultrasonic wave received with the organic piezoelectric elements. Moreover, since thermal noise becomes large if the electrical capacitance is small, a signal-to-noise ratio with respect to the obtained received signal tends to be disadvantageous.

In a case where the organic piezoelectric element is laminated on the inorganic piezoelectric element, focus misalignment or decrease in reception efficiency will occur unless the positions of their electrodes coincide with each other with respect to the direction of beam transmission. Accordingly, it is preferable that positions of electrodes of the inorganic piezoelectric element and of the organic piezoelectric element laminated on the inorganic piezoelectric element coincide with each other in the direction of beam transmission as much as possible. However, it has been difficult to achieve precise coincidence in a conventional configuration or a conventional method of producing an ultrasound probe.

Furthermore, as the temperature of the organic piezoelectric body increases, crystallinity thereof gradually decreases. Hence, the upper limit temperature for use is considerably lower than the Curie point. As typical examples, polyvinylidene fluoride (PVDF) has an upper limit temperature for use of 80° C., and a polyvinylidene fluoride trifluoroethylene copolymer (P(VDF-TrFE)) has an upper limit temperature for use of 100° C. Accordingly, if the materials are heated to a higher temperature than such temperatures during processing, ferroelectricity deteriorates, and depolarization occurs. One effective means for recovering the deteriorated ferroelectricity is repolarization. However, the coercive electric field (Ec) of the organic piezoelectric body is extremely high, such as about 400 kV/cm to about 450 kV/cm. Therefore, application of an extremely high voltage is required in order to cause, on the device, repolarization of the organic piezoelectric body that has once undergone depolarization, but application of such a high voltage is difficult from a standpoint of processing. Accordingly, when the organic piezoelectric body is laminated on the inorganic piezoelectric body, they need to be processed at the lowest possible temperature with the minimum possible heat history. However, processing with almost no heat history has been difficult in a conventional configuration or a conventional method of producing an ultrasound probe.

SUMMARY OF THE INVENTION

The present invention is aimed at solving the problem of the conventional art and has an object to provide an ultrasound probe which has an excellent acoustic transmittance of ultrasonic beams transmitted from a plurality of inorganic piezoelectric elements, while having the improved conversion efficiency and signal-to-noise ratio of the reception signal in a plurality of organic piezoelectric elements, in which positions of electrodes precisely coincide with each other in the direction of beam transmission between the inorganic piezoelectric elements for transmission and reception of ultrasonic waves and the organic piezoelectric elements exclusively for reception of ultrasonic waves, and which can maintain excellent properties of the organic piezoelectric elements even in a finished device, and another object to provide a method of producing the ultrasound probe.

The ultrasound probe according to the present invention comprises: a backing material; a plurality of inorganic piezoelectric elements arranged on a top surface of the backing material; a first acoustic matching layer separated into a plurality of pieces disposed on the plurality of inorganic piezoelectric elements; and a second acoustic matching layer separated into a plurality of pieces disposed on the first acoustic matching layer, wherein the second acoustic matching layer comprises an upper organic layer used for constituting a plurality of organic piezoelectric elements, and a lower organic layer for performing, together with the upper organic layer, acoustic matching for the plurality of inorganic piezoelectric elements.

Preferably, the upper organic layer is formed to be thinner than the lower organic layer.

Preferably, the plurality of organic piezoelectric elements comprise: the upper organic layer in a sheet form; a ground electrode layer extending over a top surface of the upper organic layer; and a signal electrode layer separated into a plurality of pieces arranged on a rear surface of the upper organic layer so as to face the lower organic layer, wherein the ultrasound probe further comprises a plurality of separating parts extending in a layered direction in parallel at a constant pitch such that each layer from the signal electrode layer through the plurality of inorganic piezoelectric elements is separated into a plurality of pieces, whereby the plurality of organic piezoelectric elements and the plurality of inorganic piezoelectric elements are arranged at a same pitch.

Preferably, the ultrasound probe further comprises sub-dicing grooves that extend in the layered direction to further sever each of the plurality of inorganic piezoelectric elements, each of pieces constituting the plurality of inorganic piezoelectric elements and the first acoustic matching layer, or each of pieces constituting the plurality of inorganic piezoelectric elements, the first acoustic matching layer and the lower organic layer in the second acoustic matching layer into a plurality of sub-dices.

Preferably, the plurality of organic piezoelectric elements are used as reception devices for receiving ultrasonic waves transmitted from the plurality of inorganic piezoelectric elements, the upper organic layer is formed to have a thickness capable of having a predetermined electrical capacitance required to convert an ultrasonic echo received into a reception signal, and the upper organic layer and the lower organic layer are formed such that a sum of their thicknesses is a value with which desired acoustic matching is performed on ultrasonic waves transmitted from the plurality of inorganic piezoelectric elements.

Preferably, the upper organic layer and the lower organic layer have acoustic impedances within a range of ±10% from each other. Preferably, the lower organic layer has an acoustic impedance larger than that of the upper organic layer and smaller than that of the first acoustic matching layer.

Preferably, the plurality of inorganic piezoelectric elements comprise: a plurality of inorganic piezoelectric bodies separated from one another; and a signal electrode layer separated into a plurality of pieces arranged on one side of the plurality of inorganic piezoelectric bodies and a ground electrode layer separated into a plurality of pieces arranged on another side of the plurality of inorganic piezoelectric bodies.

The plurality of inorganic piezoelectric bodies can be formed of a Pb-based perovskite structure oxide such as lead zirconate titanate ($Pb(Zr,Ti)O_3$) or a magnesium niobate lead titanate solid solution (PMN-PT). In addition, the upper organic layer can be formed of an organic material alone, and the lower organic layer can be formed of an organic material or a composite material of an organic material and an inorganic material. Further, the upper organic layer and the lower organic layer can be formed of a vinylidene fluoride compound such as polyvinylidene fluoride (PVDF) or polyvinylidene fluoride-trifluoroethylene copolymer (P(VDF-TrFE)).

The ultrasound probe can further comprise an acoustic lens disposed on the plurality of organic piezoelectric elements. In addition, the ultrasound probe can further comprise, between the plurality of organic piezoelectric elements and the acoustic lens, a protection layer for protecting the plurality of organic piezoelectric elements.

The ultrasound probe can further comprise amplifiers for organic piezoelectric element respectively connected with the plurality of organic piezoelectric elements.

The ultrasound probe can further comprise a light irradiation unit for emitting irradiation light beams toward a subject, wherein ultrasonic waves from a subject induced by irradiation of irradiation light beams emitted from the light irradiation unit are received by the plurality of organic piezoelectric elements or the plurality of inorganic piezoelectric elements.

The method of producing an ultrasound probe according to the present invention comprises the steps of: joining an inorganic piezoelectric element layer onto a top surface of a backing material, the inorganic piezoelectric element layer extending over the backing material; joining an acoustic matching layer onto the inorganic piezoelectric element layer, the acoustic matching layer extending over the inorganic piezoelectric element layer; joining an organic layer onto the acoustic matching layer, the organic layer extending over the acoustic matching layer, and forming a conductive layer over an entire surface of the organic layer; dicing layers including the conductive layer through the inorganic piezoelectric element layer in a layered direction at a given pitch to form and arrange a plurality of inorganic piezoelectric elements and to form, on the plurality of inorganic piezoelectric elements, pieces of a first acoustic matching layer, pieces of a lower organic layer and pieces of a signal electrode layer sequentially superposed with their positions aligned; and joining an upper organic layer onto the signal electrode layer, the upper organic layer extending over the signal electrode layer, and forming a ground electrode layer on an entire surface of the upper organic layer, thereby forming and arranging a plurality of organic piezoelectric elements each made of the signal electrode layer, the upper organic layer and the ground electrode layer.

Preferably, the upper organic layer and the lower organic layer constitute a second acoustic matching layer and are formed such that the sum of their thicknesses is near a value satisfying the $\lambda/4$ resonance condition when the fundamental waves transmitted from the inorganic piezoelectric elements have a wavelength $\lambda$.

The method of producing an ultrasound probe can further comprise the step of, after joining the inorganic piezoelectric layer onto the top surface of the backing material, sub-dicing the inorganic piezoelectric layer in the layered direction so as to further sever each of the plurality of inorganic piezoelectric elements, thereby forming a plurality of sub-dices in each of the plurality of inorganic piezoelectric elements.

According to the present invention, a second acoustic matching layer comprises an upper organic layer, which constitutes a plurality of organic piezoelectric elements, and a lower organic layer for, together with the upper organic layer, performing acoustic matching for a plurality of inorganic piezoelectric elements. Hence, excellent acoustic transmittance of ultrasonic beams transmitted from the inorganic piezoelectric elements is secured, while acquisition efficiency of reception signals generated in the organic piezoelectric elements can be improved, and the signal-to-noise ratio can also be improved.

In addition, positions of electrodes can precisely coincide with each other between the inorganic piezoelectric elements for transmission and reception of ultrasonic waves and the organic piezoelectric elements exclusively for reception of ultrasonic waves, and, in addition, excellent properties of the organic piezoelectric elements can be maintained even in a finished device.

DETAILED DESCRIPTION OF THE INVENTION

The embodiment of the present invention will be described below based on the appended drawings.

Figure 1:
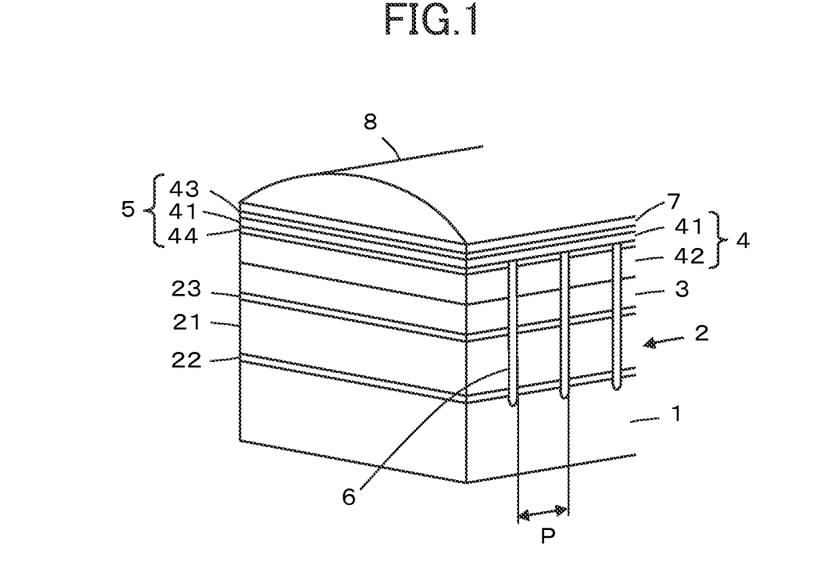
FIG. 1 is a perspective view illustrating a part of an ultrasound probe according to an embodiment of the present invention.
Figure 2:
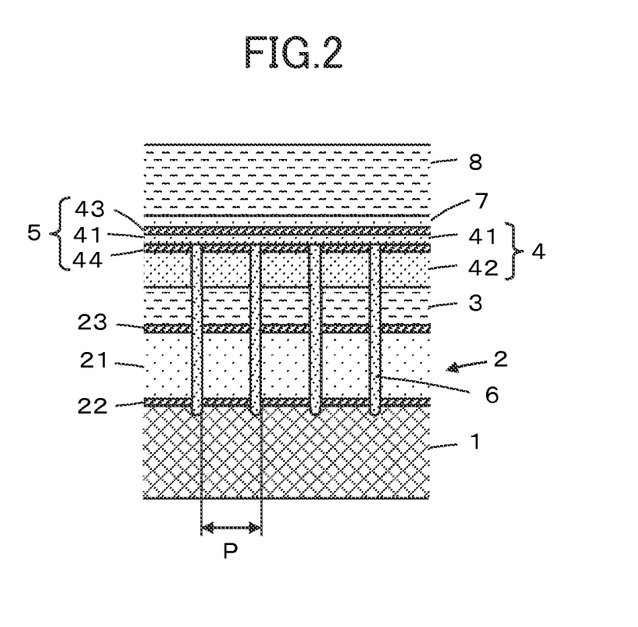
FIG. 2 is a cross section illustrating a constitution of the ultrasound probe according to the embodiment.

FIGS. 1 and 2 illustrate a configuration of an ultrasound probe according to the embodiment of the invention.

A plurality of inorganic piezoelectric elements 2 are arranged at a pitch of P on the top surface of a backing material 1. The inorganic piezoelectric elements 2 comprise a plurality of inorganic piezoelectric bodies 21 separated from one another. Each of the inorganic piezoelectric elements 2 has a signal electrode layer 22 joined to one face of the inorganic piezoelectric bodies 21 and a ground electrode layer 23 joined to the other face of the inorganic piezoelectric bodies 21. Thus, each inorganic piezoelectric element 2 comprises a dedicated inorganic piezoelectric body 21, a dedicated signal electrode layer 22, and a dedicated ground electrode layer 23.

A first acoustic matching layer 3 is joined onto the inorganic piezoelectric elements 2. The first acoustic matching layer 3 is separated into a plurality of pieces which are arranged at the same pitch of P as that of the inorganic piezoelectric elements 2.

It is preferable that each of the pieces constituting the inorganic piezoelectric elements 2 be severed into a plurality of sub-dices. For example, sub-dicing grooves may be formed to extend in the layered direction such that each piece of the inorganic piezoelectric bodies 21, each piece of the signal electrode layer 22 and each piece of the ground electrode layer 23 (of the inorganic piezoelectric elements 2), or each piece of the inorganic piezoelectric bodies 21, each piece of the signal electrode layer 22, each piece of the ground electrode layer 23 and each piece of the first acoustic matching layer 3 are further severed into a plurality of pieces. Alternatively, sub-dicing grooves may be formed to extend in the layered direction such that each piece of the inorganic piezoelectric bodies 21, each piece of the signal electrode layer 22, each piece of the ground electrode layer 23, each piece of the first acoustic matching layer 3 and each piece of lower organic layer 42 are further severed into a plurality of pieces.

In this case, one or two sub-dicing grooves are preferably formed in each of the inorganic piezoelectric elements 2 to thereby form two or three sub-dices. In this manner, a plurality of sub-dices are formed, whereby the piezoelectric constant of the inorganic piezoelectric elements 2 can be increased, and transmission and reception sensitivity of the ultrasound probe can be improved.

A second acoustic matching layer 4 is joined onto the first acoustic matching layer 3. The second acoustic matching layer 4 comprises an upper organic layer 41 and the lower organic layer 42.

The lower organic layer 42 is separated into a plurality of pieces that are arranged on the first acoustic matching layer 3 at the same pitch of P as that of the plurality of inorganic piezoelectric elements 2. The upper organic layer 41, on the other hand, is sheet-shaped, not separated into a plurality of pieces and extends over the entire lower organic layer 42. The upper organic layer 41 and the lower organic layer 42 are formed such that the sum of their thicknesses becomes a value with which the desired acoustic matching is performed on the ultrasonic waves transmitted from the inorganic piezoelectric elements. For example, the upper organic layer 41 and the lower organic layer 42 are formed such that the sum of their thicknesses is in a vicinity of a value satisfying the λ/4 resonance condition when the fundamental waves of ultrasonic waves from the inorganic piezoelectric elements 2 (central frequency in a band of −6 dB from the maximum sensitivity of the inorganic piezoelectric body 21) have a wavelength λ, whereby the second acoustic matching layer 4 including the upper organic layer 41 and the lower organic layer 42 together has an excellent acoustic transmittance of the ultrasonic waves transmitted from the inorganic piezoelectric elements.

Moreover, the upper organic layer 41 constitutes a plurality of organic piezoelectric elements 5. That is, the upper organic layer 41 is provided with a ground electrode layer 43 joined onto and extending over the top surface thereof, and with a signal electrode layer 44 that is separated into a plurality of pieces at the same pitch of P as that of the inorganic piezoelectric elements 2 and are joined onto the rear surface thereof facing the lower organic layer 42. Accordingly, the upper organic layer 41 serves as organic piezoelectric bodies of the organic piezoelectric elements 5. Each of the organic piezoelectric elements 5 thus formed and arranged comprises a dedicated piece of the signal electrode layer 44 and the common upper organic layer 41 and the common ground electrode layer 43. Therefore, the pitch at which the organic piezoelectric elements 5 are arranged is determined only by the pitch at which the pieces of the signal electrode layer 44 joined onto the rear surface of the upper organic layer 41 are arranged, and the organic piezoelectric elements 5 are arranged at the same pitch of P as that of the inorganic piezoelectric elements 2.

A plurality of pieces of the inorganic piezoelectric elements 2, of the first acoustic matching layer 3, of the lower organic layer 42 of the second acoustic matching layer 4, and of the signal electrode layer 44 separated at the same pitch of P are arrayed in the layered direction with their positions being aligned with one another, and a filler is filled between the columns of the layers to thereby form separating parts 6 which separate the stacked pieces constituting the layers including the inorganic piezoelectric elements 2 through the signal electrode layer 44 from one another. That is, the separating parts 6 extend in parallel at the same pitch of P in the layered direction so as to penetrate through the layers including the top surface of the signal electrode layer 44 to the top surface of the backing material 1.

Further, an acoustic lens 8 is joined onto the organic piezoelectric elements 5 through the intermediary of a protection layer 7.

The inorganic piezoelectric body 21 of the inorganic piezoelectric element 2 is formed of an inorganic piezoelectric body forming material such as a lead-based perovskite structure oxide. For example, the inorganic piezoelectric body 21 can be formed of a lead-based piezoelectric ceramic typified by lead zirconate titanate ($Pb(Zr,Ti)O_3$) or a relaxor-based piezoelectric monocrystal typified by a magnesium niobate-lead titanate solid solution (PMN-PT) and a zinc niobate-lead titanate solid solution (PZN-PT). On the other hand, the upper organic layer 41 of the organic piezoelectric element 5 is formed of an organic piezoelectric body forming material such as a vinylidene fluoride (VDF) material. For example, the upper organic layer 41 can be made of a polymer piezoelectric element such as polyvinylidene fluoride (PVDF) or a polyvinylidene fluoride trifluoroethylene copolymer (P(VDF-TrFE)).

The backing material 1 supports the inorganic piezoelectric elements 2 and absorbs the ultrasonic waves discharged backwards. The backing material 1 may be made of a rubber material such as ferrite rubber.

The first acoustic matching layer 3 is provided to allow ultrasonic beams emitted from the inorganic piezoelectric elements 2 to efficiently enter a subject and is formed of a material having an acoustic impedance between that of the inorganic piezoelectric elements 2 and that of a living body.

The second acoustic matching layer 4 is provided to allow an ultrasonic beam emitted from the inorganic piezoelectric elements 2 to efficiently enter a subject, and the lower organic layer 42 is formed of an organic material or a composite material of an organic material and an inorganic material. For example, the lower organic layer 42 can be formed of an organic material including a vinylidene fluoride (VDF) material such as polyvinylidene fluoride (PVDF) or polyvinylidene fluoride-trifluoroethylene copolymer (P(VDF-TrFE)) used to form the upper organic layer 41. In addition, the lower organic layer 42 can also be formed of a composite material of an organic material and an inorganic material in which zirconia particles are dispersed in an epoxy resin, for example.

The upper organic layer 41 and the lower organic layer 42 are preferably formed of materials having the same acoustic impedance or close acoustic impedances to each other. As an example, if the acoustic impedances of the two layers fall within the range of ±10% from each other, the second acoustic matching layer 4 can be constituted with no influence on acoustic matching of ultrasonic waves. Furthermore, the lower organic layer 42 can also be formed of a material having an acoustic impedance higher than that of the upper organic layer 41 and, at the same time, smaller than that of the first acoustic matching layer 3.

The filler to form the separating parts 6 is used to secure the positions and postures of the adjacent pieces and is made of, for example, an epoxy resin.

The protection layer 7 protects the ground electrode layer 43 of the organic piezoelectric elements 5 and is made of, for example, polyvinylidene fluoride (PVDF). Unless protection of the ground electrode layer 43 is impaired, the acoustic lens 8 can be directly joined onto the organic piezoelectric elements 5 without forming the protection layer 7.

The acoustic lens 8 uses refraction to focus an ultrasonic beam in order to improve the resolution in the elevation direction. The acoustic lens 8 is formed of, for example, silicon rubber.

Next, the operation of this embodiment will be described.

In the operation, the inorganic piezoelectric elements 2 are used as vibrators provided exclusively for transmission of ultrasonic waves, while the organic piezoelectric elements 5 are used as vibrators provided exclusively for reception of ultrasonic waves.

Application of a voltage in the form of pulses or a continuous wave between the signal electrode layer 22 and the ground electrode layer 23 of the inorganic piezoelectric elements 2 causes the inorganic piezoelectric bodies 21 of the inorganic piezoelectric elements 2 to expand and contract, generating ultrasonic waves in the form of pulses or a continuous wave. The ultrasonic waves pass through the first acoustic matching layer 3, the second acoustic matching layer 4, the protection layer 7, and the acoustic lens 8 to enter a subject, where the ultrasonic waves are combined to form an ultrasonic beam, which propagates inside the subject.

Subsequently, as ultrasonic echoes that propagated inside and reflected from the subject enter the individual organic piezoelectric elements 5 through the acoustic lens 8 and the protection layer 7, the upper organic layer 41 sensitively responds to the harmonic components of the ultrasonic waves by expansion and contraction, generating electric signals between the signal electrode layer 44 and the ground electrode layer 43, which electric signals are outputted as reception signals.

Accordingly, based on the reception signals outputted from the organic piezoelectric elements 5, a harmonic image can be produced. Since the inorganic piezoelectric elements 2 and the organic piezoelectric elements 5 are arranged at the same pitch of P with their respective positions being aligned to each other in the layered direction, an ultrasonic echo from the subject can be received at the same position as the transmission position of the ultrasonic beam, whereby a harmonic image can be produced with a high accuracy.

The inorganic piezoelectric elements 2 may be used as vibrators for both transmission and reception of the ultrasonic waves. In that case, ultrasonic echoes received by the organic piezoelectric elements 5 through the acoustic lens 8 and the protection layer 7 further travel through the second acoustic matching layer 4 and the first acoustic matching layer 3 to enter the individual inorganic piezoelectric elements 2, whereupon the inorganic piezoelectric bodies 21 respond mainly to the fundamental wave components of the ultrasonic waves by expansion and contraction, generating electric signals between the signal electrode layer 22 and the ground electrode layer 23.

Thus, a compound image of fundamental wave components and harmonic components can be produced based on the reception signals corresponding to the fundamental wave components obtained from the inorganic piezoelectric elements 2 and the reception signals corresponding to the harmonic components obtained from the organic piezoelectric elements 5.

Also in this case, since the inorganic piezoelectric elements 2 and the organic piezoelectric elements 5 are arranged at the same pitch of P with their respective positions being aligned to each other in the layered direction, the fundamental wave components and the harmonic components of the ultrasonic echoes can be received at the same arrangement positions, and a compound image in which fundamental wave components and harmonic components are precisely combined can be produced.

An ultrasound probe as described above can be produced as follows.

Figure 3A:
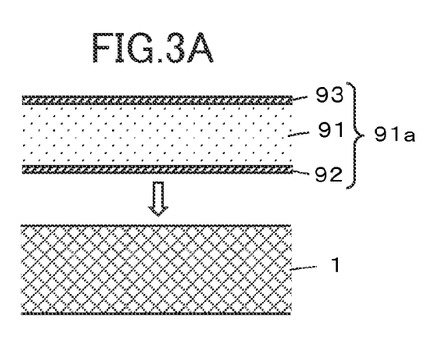
FIGS. 3A to 3E are cross sections illustrating a method of producing the ultrasound probe according to the embodiment in order of production steps.

First, as illustrated in FIG. 3A, an inorganic piezoelectric element layer 91*a* extending over the whole area of the backing material 1 is joined onto the surface of the backing material 1 with, for example, an adhesive. The inorganic piezoelectric element layer 91*a* is formed of an inorganic piezoelectric body layer 91 which extends over the whole area of the backing material 1 and is provided over the whole surface thereof on respective sides with conductive layers 92 and 93.

Figure 3B:
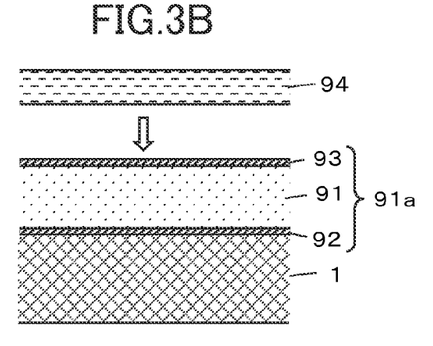

Next, as illustrated in FIG. 3B, an acoustic matching layer 94 extending over the whole area of the inorganic piezoelectric element layer 91*a* is joined onto the conductive layer 93 at a temperature of 80° C. to 100° C., for example. In the case where sub-dices of the inorganic piezoelectric bodies 21 are formed at this time, the inorganic piezoelectric element layer 91*a* or the respective layers including the inorganic piezoelectric element layer 91*a* through the acoustic matching layer 94 are diced in the layered direction, thereby forming sub-dicing grooves.

Figure 3C:
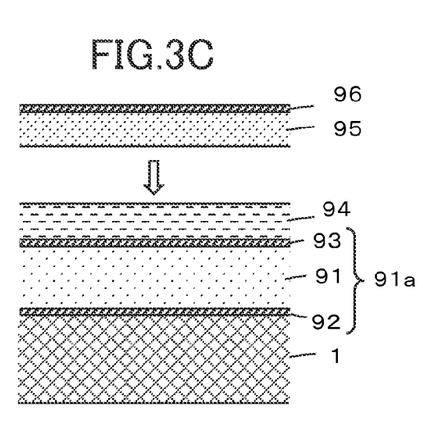

Then, as illustrated in FIG. 3C, an organic layer 95 is joined onto the acoustic matching layer 94. The organic layer 95 is large enough to extend over the whole surface of the acoustic matching layer 94 and previously provided with a conductive layer 96 on the whole surface thereof opposite from the surface facing the acoustic matching layer 94.

Figure 3D:
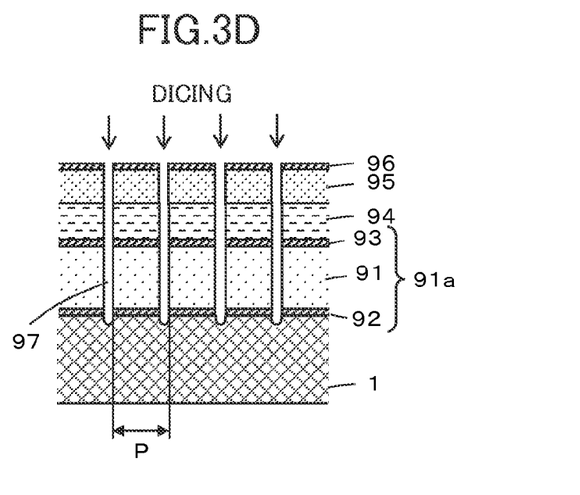

Subsequently, as illustrated in FIG. 3D, the conductive layer 96, the organic layer 95, the acoustic matching layer 94 and the inorganic piezoelectric element layer 91*a* are each subjected to dicing at the pitch of P to be thereby severed into a plurality of pieces. Since dicing is performed such that the respective layers including the conductive layer 96 through the inorganic piezoelectric element layer 91*a* are each completely severed into pieces, the thus severed pieces of the respective layers are arranged with their positions being aligned in the layered direction. Accordingly, the inorganic piezoelectric elements 2 are arranged at the arrangement pitch of P on the surface of the backing material 1, and each piece of the first acoustic matching layer 3, each piece of the lower organic layer 42 and each piece of the signal electrode layer 44 are formed to be aligned and sequentially superposed on one another on each inorganic piezoelectric element 2. In addition, resulting from dicing, a plurality of grooves 97 in a flat plate shape penetrating through the respective layers in the layered direction are formed at the pitch of P between columns of pieces of the respective layers stacked in the layered direction.

As described above, by dicing the respective layers including the conductive layer 96 through the inorganic piezoelectric element layer 91*a* at the pitch of P, each of the layers can be readily severed into a plurality of pieces and, at the same time, the pieces of the respective layers can be aligned in the layered direction. The signal electrode layers 44 of the organic piezoelectric elements 5, the signal electrode layer 22 of the inorganic piezoelectric elements 2 and the ground electrode layer 23 of the inorganic piezoelectric elements 2 can be precisely aligned to one another.

Figure 3E:
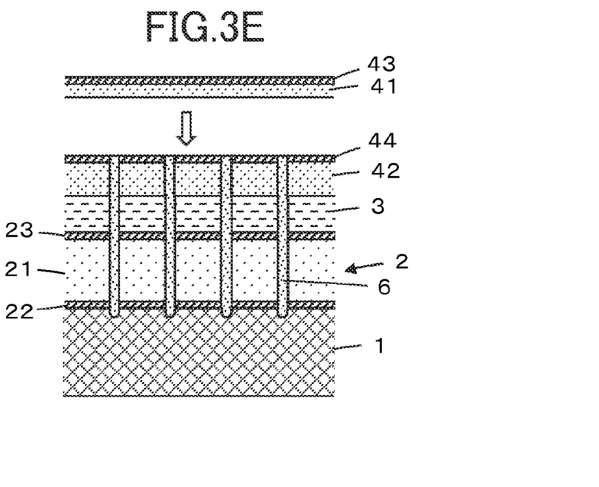

Then, the grooves 97 formed by dicing are filled with a filler, and as illustrated in FIG. 3E, the separating parts 6 for fixing the positions and postures of the pieces of the respective layers are formed, and thereafter the upper organic layer 41 is pressure-bonded onto the signal electrode layer 44 at a temperature of 80° C., for example. The upper organic layer 41 is large enough to extend over the whole signal electrode layer 44 and preliminarily provided with the ground electrode layer 43 on the whole surface thereof opposite from the surface facing the signal electrode layer 44.

The upper organic layer 41 constitutes a part of the second acoustic matching layer 4 for acoustic matching of ultrasonic waves transmitted from the inorganic piezoelectric elements 2, and the upper organic layer 41 and the lower organic layer 42 only need to be formed such that their total thickness has a value with which the desired acoustic matching of ultrasonic waves transmitted from the inorganic piezoelectric elements 2 is performed. Taking up the upper organic layer 41 alone, the upper organic layer 41 can be thin in order to improve the electrical capacitance of the organic piezoelectric elements 5 with no restriction for acoustic matching. That is, the upper organic layer 41 is formed to have a desired thickness capable of having an electrical capacitance which allows the ultrasonic echoes received by the organic piezoelectric elements 5 to be efficiently converted into reception signals, and the thickness of the upper organic layer 41 is added with the thickness of the lower organic layer 42. Accordingly, the upper organic layer 41 and the lower organic layer 42 are formed such that their total thickness falls within a range in which acoustic matching of ultrasonic waves transmitted from the inorganic piezoelectric elements 2 is performed. In this manner, the upper organic layer 41 is formed to be thinner than the lower organic layer 42, whereby the second acoustic matching layer 4 can be formed to be capable of performing acoustic matching of ultrasonic waves transmitted from the inorganic piezoelectric elements 2, while the organic piezoelectric elements 5 can be formed thinly. It is preferable that the upper organic layer 41 and the lower organic layer 42 be formed such that the sum of their thicknesses is near a value satisfying the $\lambda/4$ resonance condition when the fundamental waves transmitted from the inorganic piezoelectric elements 2 have a wavelength $\lambda$.

Further, as the temperature of the upper organic layer 41 increases, crystallinity thereof gradually decreases. Hence, the upper limit temperature of the upper organic layer 41 for use is considerably lower than the Curie point. Although application of a high temperature of 80° C. to 100° C. used for laminating the layers such as the acoustic matching layer 94 easily causes depolarization, the upper organic layer 41 is laminated after the other layers except the protection layer 7 and the acoustic lens 8 are laminated. Hence, the upper organic layer 41 is not exposed to high temperature when the other layers are laminated or the grooves 97 are filled with a filler, whereby depolarization can be suppressed.

In addition, since the upper organic layer 41 is not present until the layers underneath the upper organic layer 41, i.e., the signal electrode layer 22, the inorganic piezoelectric bodies 21, the ground electrode layer 23, the first acoustic matching layer 3, the lower organic layer 42 and the signal electrode layer 44 are adhered sequentially, these layers can be adhered at a high temperature and laminated with a high adhesive force.

After the upper organic layer 41 is laminated onto the signal electrode layer 44 in this manner, the acoustic lens 8 is joined onto the ground electrode layer 43 of the organic piezoelectric elements 5 through the intermediary of the protection layer 7 to produce the ultrasound probe as illustrated in FIGS. 1 and 2.

In an example of producing a linear probe in which ultrasonic waves transmitted from the inorganic piezoelectric elements 2 have a frequency of about 7 MHz, the first acoustic matching layer 3 has an acoustic impedance of about 8.9 Mrayl (kg/m$^2$s), and the second acoustic matching layer 4 has an acoustic impedance of about 4.0 Mrayl, the inorganic piezoelectric body 21 is formed using lead zirconate titanate (Pb(Zr,Ti)O$_3$) to have a thickness of about 190 μm, whereby the first acoustic matching layer 3 having a thickness of about 80 μm can be formed. Then, using PVDF, the lower organic layer 42 and the upper organic layer 41 are formed to have a thickness of about 60 μm and a thickness of about 20 μm, respectively, whereby the second acoustic matching layer 4 as a whole has a thickness of about 80 μm. Accordingly, the organic piezoelectric elements 5 having a desired thickness can be formed, while the second acoustic matching layer 4 satisfies the resonance condition for the inorganic piezoelectric elements 2.

When using a composite material of an organic material and an inorganic material to form the lower organic layer 42 of the second acoustic matching layer 4, the upper organic layer 41 is formed of polyvinylidene fluoride-trifluoroethylene copolymer (P(VDF-TrFE)) to have a thickness of about 10 μm, and the lower organic layer 42 is formed of an epoxy resin, in which zirconia particles are dispersed to achieve an acoustic impedance of about 5 to 6 Mrayl, to have a thickness of about 70 μm, for example. The first acoustic matching layer 3 is formed of an epoxy resin, in which zirconia particles are dispersed to achieve an acoustic impedance of about 8 Mrayl, to have a thickness of about 100 μm. By forming the first acoustic matching layer 3 and the second acoustic layer 4 in this manner, the organic piezoelectric elements 5 can be formed to have a desired thickness, while the second acoustic matching layer 4 satisfies the resonance condition for the inorganic piezoelectric elements 2.

As described above, the second acoustic matching layer 4 has a two-layered structure having the upper organic layer 41 and the lower organic layer 42, the upper organic layer 41 used for constituting the organic piezoelectric elements 5 is formed to have a desired thickness, while the second acoustic matching layer 4 is formed such that the total thickness of the upper organic layer 41 and the lower organic layer 42 satisfies the resonance condition. As a result, the organic piezoelectric elements 5 can have an improved efficiency of acquiring reception signals, while excellent acoustic transmittance of ultrasonic beams transmitted from the inorganic piezoelectric elements is maintained.

In addition, since the inorganic piezoelectric elements 2 and the organic piezoelectric elements 5 are arranged with their positions being aligned to each other, a high-precision harmonic image and a high-precision compound image can be produced.

Moreover, since the upper organic layer 41 that works as the organic piezoelectric body of the organic piezoelectric elements 5 is hardly exposed to high temperature during production of an ultrasound probe, depolarization of the upper organic layer 41 can be suppressed.

Figure 4:
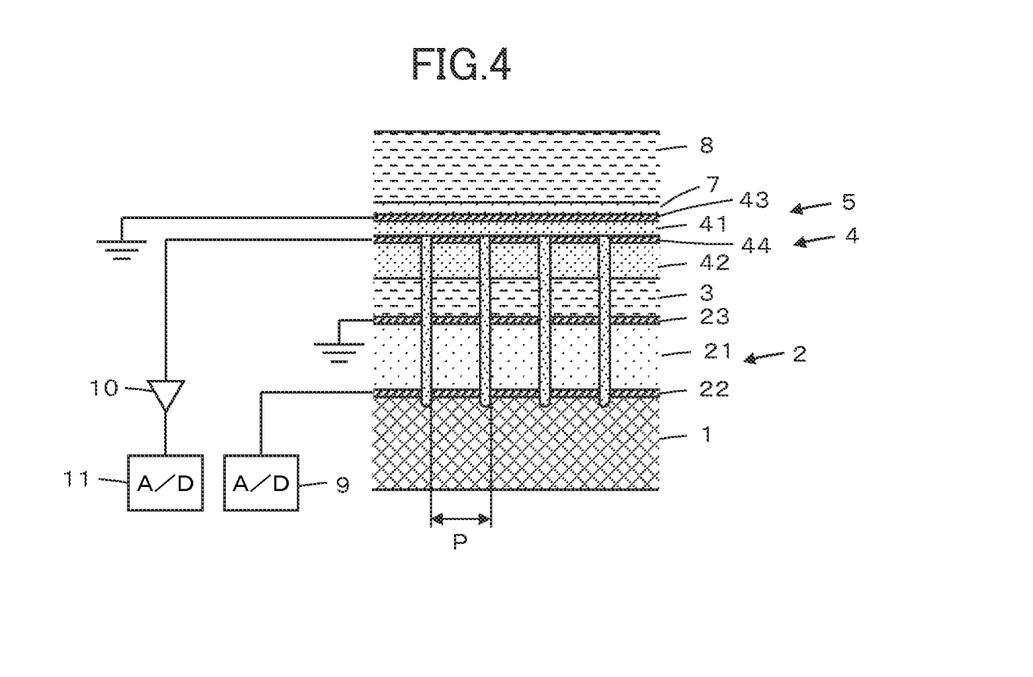
FIG. 4 is a cross section illustrating a constitution of an ultrasound probe according to a variation of the embodiment.

As illustrated in FIG. 4, the signal electrode layer 22 in each of the inorganic piezoelectric elements 2 can be connected with an A/D converter 9 for inorganic piezoelectric element, whereas the signal electrode layer 44 in each of the organic piezoelectric elements 5 can be connected with an amplifier 10 for organic piezoelectric element and an A/D converter 11 for organic piezoelectric element.

An electrical capacitance of the organic piezoelectric elements 5 can be improved by designing the organic piezoelectric body to have a thin thickness as described above. However, it is still difficult to acquire a reception signal having sufficient intensity merely by such design, and it is necessary to amplify the reception signal with the amplifier 10 for organic piezoelectric element. At this time, in order to prevent the reception signal from attenuating in the course of transmission from the organic piezoelectric elements 5 to the amplifier 10 for organic piezoelectric element, the amplifier 10 for organic piezoelectric element is preferably connected in the vicinity of or directly with the signal electrode layer 44 in the organic piezoelectric elements 5.

In addition, by providing a multiplexer in the ultrasound probe, the number of signal lines led out from the ultrasound probe can be decreased. For example, a multiplexer is arranged downstream of the A/D converter 9 for inorganic piezoelectric element and the A/D converter 11 for organic piezoelectric element, whereby two signal lines led out from the A/D converter 9 for inorganic piezoelectric element and the A/D converter 11 for organic piezoelectric element can be unified into a single signal line.

While it has been described that the lower organic layer 95 previously provided on the surface thereof with the conductive layer 96 is joined onto the first acoustic matching layer 94, the invention is not limited thereto; the lower organic layer 95 may be first joined onto the first acoustic matching layer 94, with the conductive layer 96 thereafter formed on the surface of the lower organic layer 95.

While the upper organic layer 41 previously provided on the top surface thereof with the ground electrode layer 43 is joined onto the signal electrode layer 44, the upper organic layer 41 may be first joined onto the signal electrode layer 42, followed by formation of the ground electrode layer 43 on the top surface of the upper organic layer 41.

Figure 5:
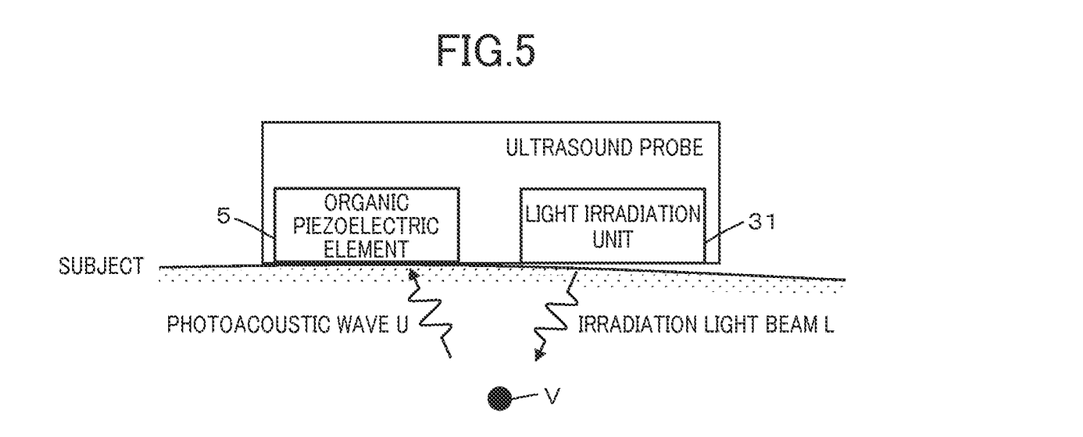
FIG. 5 is a view illustrating a constitution of an ultrasound probe according to another variation of the embodiment.

In the above-described embodiment, ultrasonic waves generated by the inorganic piezoelectric elements 2 are transmitted toward the subject, and ultrasonic echoes reflected in the subject are received by the inorganic piezoelectric elements 2 or the organic piezoelectric elements 5. However, by providing a light irradiation unit 31 for irradiating the subject with an irradiation light beam L as illustrated in FIG. 5, the irradiation light beam L can be emitted toward the subject by the light irradiation unit 31, and also a photoacoustic wave U (ultrasonic wave) from the subject induced by irradiation of the irradiation light beam L can be received, for example, by the organic piezoelectric elements 5. In this manner, the inside of the subject can be imaged using the photoacoustic effect; so-called photoacoustic imaging (PAI) can be performed.

The light irradiation unit 31 sequentially emits the plural irradiation light beams L having different wavelengths from one another toward the subject and comprises a semiconductor laser (LD), a light emitting diode (LED), a solid laser, a gas laser or the like. The light irradiation unit 31 uses, for example, pulsed laser light beams as irradiation light beams L and emits pulsed laser light beams toward the subject, as sequentially changing the wavelength for each pulse.

During photoacoustic imaging, the light irradiation unit 31 emits irradiation light beams L toward the subject, and once a predetermined living tissue V inside the subject is irradiated with the irradiation light beams L, the living tissue V absorbs light energy of the irradiation light beams L to thereby release photoacoustic waves U (ultrasonic waves) that are elastic waves.

For example, the irradiation light beam L having a wavelength of about 750 nm and the irradiation light beam L having a wavelength of about 800 nm are emitted from the light irradiation unit 31 sequentially toward the subject. In the meantime, oxygenated hemoglobin (hemoglobin combined with oxygen; oxy-Hb) included in plenty in a human artery has a higher coefficient of molecular absorption for the irradiation light beam L with a wavelength of 750 nm than for the irradiation light beam L with a wavelength of 800 nm. On the other hand, deoxygenated hemoglobin (hemoglobin not combined with oxygen; deoxy-Hb) included in plenty in a human vein has a lower coefficient of molecular absorption for the irradiation light beam L with a wavelength of 750 nm than for the irradiation light beam L with a wavelength of 800 nm. Accordingly, if an artery and a vein are irradiated with the irradiation light beams L having wavelengths of 800 nm and 750 nm respectively, photoacoustic waves U having intensities corresponding to the respective coefficients of molecular absorption of the artery and the vein will be released.

The photoacoustic waves U released from an artery or a vein are received with the organic piezoelectric elements 5 of the ultrasound probe similarly to the embodiment described above.

Accordingly, the ultrasound probe can be used not only for an ultrasound image but also for a photoacoustic image. Hence, a variety of ultrasound examinations can be performed by using a single ultrasound probe.

The photoacoustic waves U from the subject induced by irradiation of irradiation light beams L can be received also by the inorganic piezoelectric elements 2.

What is claimed is:

1. An ultrasound probe comprising:
   a backing material;
   a plurality of inorganic piezoelectric elements arranged on a top surface of the backing material;
   a first acoustic matching layer separated into a plurality of pieces disposed on the plurality of inorganic piezoelectric elements; and
   a second acoustic matching layer disposed on the first acoustic matching layer,
   wherein the second acoustic matching layer comprises an upper organic layer used for constituting a plurality of organic piezoelectric elements, and a lower organic layer separated into a plurality of pieces for performing, together with the upper organic layer, acoustic matching for the plurality of inorganic piezoelectric elements,
   wherein the plurality of organic piezoelectric elements comprise:
   the upper organic layer in a sheet form;
   a ground electrode layer extending over a top surface of the upper organic layer; and
   a signal electrode layer separated into a plurality of pieces arranged on a rear surface of the upper organic layer so as to face the lower organic layer,
   wherein the ultrasound probe further comprises a plurality of separating parts extending in a layered direction in parallel at a constant pitch such that each layer from the signal electrode layer through the plurality of inorganic piezoelectric elements is separated into a plurality of pieces, whereby the plurality of organic piezoelectric elements and the plurality of inorganic piezoelectric elements are arranged at a same pitch.

2. The ultrasound probe according to claim 1, wherein the upper organic layer is formed to be thinner than the lower organic layer.

3. The ultrasound probe according to claim 1, further comprising sub-dicing grooves that extend in the layered direction to further sever each of the plurality of inorganic piezoelectric elements, each of pieces constituting the plurality of inorganic piezoelectric elements and the first acoustic matching layer, or each of pieces constituting the plurality of inorganic piezoelectric elements, the first acoustic matching layer and the lower organic layer in the second acoustic matching layer into a plurality of sub-dices.

4. The ultrasound probe according to claim 1, wherein
   the plurality of organic piezoelectric elements are used as reception devices for receiving ultrasonic waves transmitted from the plurality of inorganic piezoelectric elements,
   the upper organic layer is formed to have a thickness capable of having a predetermined electrical capacitance required to convert an ultrasonic echo received into a reception signal, and
   the upper organic layer and the lower organic layer are formed such that a sum of their thicknesses is a value with which desired acoustic matching is performed on ultrasonic waves transmitted from the plurality of inorganic piezoelectric elements.

5. The ultrasound probe according to claim 1, wherein the upper organic layer and the lower organic layer have acoustic impedances within a range of ±10% from each other.

6. The ultrasound probe according to claim 1, wherein the lower organic layer has an acoustic impedance larger than that of the upper organic layer and smaller than that of the first acoustic matching layer.

7. The ultrasound probe according to claim 1, wherein the plurality of inorganic piezoelectric elements comprise:
   a plurality of inorganic piezoelectric bodies separated from one another; and
   a signal electrode layer separated into a plurality of pieces arranged on one side of the plurality of inorganic piezoelectric bodies and a ground electrode layer separated into a plurality of pieces arranged on another side of the plurality of inorganic piezoelectric bodies.

8. The ultrasound probe according to claim 7, wherein the plurality of inorganic piezoelectric bodies are formed of a lead-based perovskite structure oxide.

9. The ultrasound probe according to claim 1, wherein
   the upper organic layer is formed of an organic material alone, and
   the lower organic layer is formed of an organic material or a composite material of an organic material and an inorganic material.

10. The ultrasound probe according to claim 9, wherein the upper organic layer and the lower organic layer are formed of a vinylidene fluoride material.

11. The ultrasound probe according to claim 1, further comprising an acoustic lens disposed on the plurality of organic piezoelectric elements.

12. The ultrasound probe according to claim 11, further comprising, between the plurality of organic piezoelectric elements and the acoustic lens, a protection layer for protecting the plurality of organic piezoelectric elements.

13. The ultrasound probe according to claim 1, further comprising amplifiers for organic piezoelectric element respectively connected with the plurality of organic piezoelectric elements.

14. The ultrasound probe according to claim 1, further comprising a light irradiation unit for emitting irradiation light beams toward a subject,
   wherein ultrasonic waves from a subject induced by irradiation of irradiation light beams emitted from the light irradiation unit are received by the plurality of organic piezoelectric elements or the plurality of inorganic piezoelectric elements.

15. A method of producing an ultrasound probe comprising the steps of:
- joining an inorganic piezoelectric element layer onto a top surface of a backing material, the inorganic piezoelectric element layer extending over the backing material;
- joining an acoustic matching layer onto the inorganic piezoelectric element layer, the acoustic matching layer extending over the inorganic piezoelectric element layer;
- joining an organic layer onto the acoustic matching layer, the organic layer extending over the acoustic matching layer, and forming a conductive layer over an entire surface of the organic layer;
- dicing layers including the conductive layer through the inorganic piezoelectric element layer in a layered direction at a given pitch to form and arrange a plurality of inorganic piezoelectric elements and to form, on the plurality of inorganic piezoelectric elements, pieces of a first acoustic matching layer, pieces of a lower organic layer and pieces of a signal electrode layer sequentially superposed with their positions aligned; and
- joining an upper organic layer onto the signal electrode layer, the upper organic layer extending over the signal electrode layer, and forming a ground electrode layer on an entire surface of the upper organic layer, thereby forming and arranging a plurality of organic piezoelectric elements each made of the signal electrode layer, the upper organic layer and the ground electrode layer.

16. The method of producing an ultrasound probe according to claim 15, wherein the upper organic layer and the lower organic layer constitute a second acoustic matching layer, and the upper organic layer and the lower organic layer are formed such that a sum of their thicknesses is a value with which a desired acoustic matching is performed on ultrasonic waves transmitted from the plurality of inorganic piezoelectric elements.

17. The method of producing an ultrasound probe according to claim 15, wherein the upper organic layer is formed to be thinner than the lower organic layer.

18. The method of producing an ultrasound probe according to claim 15, further comprising the step of, after joining the inorganic piezoelectric layer onto the top surface of the backing material, sub-dicing the inorganic piezoelectric layer in the layered direction so as to further sever each of the plurality of inorganic piezoelectric elements, thereby forming a plurality of sub-dices in each of the plurality of inorganic piezoelectric elements.

* * * * *